US006048686A

United States Patent [19]

Lyday

[11] Patent Number: 6,048,686

[45] Date of Patent: Apr. 11, 2000

[54] HYPERTHERMIA AND IMMUNOTHERAPY FOR CANCER

[75] Inventor: Bruce William Lyday, Garden Grove, Calif.

[73] Assignee: Randy Kyle Brown, Bellflower, Calif.

[21] Appl. No.: 09/073,322

[22] Filed: May 5, 1998

[51] Int. Cl.[7] .......................... C12Q 1/70; A61K 39/193

[52] U.S. Cl. .......................................... 435/5; 424/218.1

[58] Field of Search ............................. 435/5; 424/218.1

*Primary Examiner*—Hankyel Park

*Assistant Examiner*—Territa Gray

*Attorney, Agent, or Firm*—Knobbe, Martens, Olson & Bear, LLP

[57] ABSTRACT

An improved method of inducing whole-body hyperthermia and enhanced anti-tumor immune response through inoculation of a fever virus with nil mortality and subsequent injection of irradiated tumor cells derived from the patient. This therapy will safely reduce the tumor burden by 90–99.9% by physical means (fever), before raising interferon levels to over 250 times baseline. The Activated Lymphokine Killer cells produced by these high interferon levels are capable of killing any cell expressing viral or tumor antigens, even those which had previously escaped immune surveillance. As a final step in the process, a specific class of Cytotoxic T Lymphocytes programmed to destroy the patient's own cancer cells will be produced by repeated inoculation of irradiated cancer cells harvested from the patient. Through a combination of three methods of therapy never previously integrated into a single regimen, it is logical to state that this therapy has a high probability of completely eradicating cancer cells from the patient. In addition, this therapy provides for life-long immunity to the reoccurrence of the disease. It is understood that the examples and embodiments described herein are for illustrative purposes only and that various changes or modifications in light thereof will be suggested to persons skilled in the art and are to be included within the spirit and purview of this application and scope of the appended claims.

6 Claims, No Drawings

HYPERTHERMIA AND IMMUNOTHERAPY FOR CANCER

BACKGROUND

1. Field of Invention

This invention relates to hyperthermia and immunotherapy for treatment of cancer.

2. Description of Prior Art

The earliest references to treating cancer with hyperthernia can be found in Egyptian papyrus scrolls dated back to 3000 BC describing a breast cancer patient treated with immersion in hot water. Total body hyperthermia in the form of hyperpyrexia (fever) has produced dramatic tumor regressions and even cures following infection with pyrogenic bacteria. In the late 19$^{th}$ and early 20$^{th}$ centuries Dr. William Coley reviewed cases of spontaneous tumor regression and discovered that a common factor was a prolonged fever in excess of 39.5 degrees C. or 103.5 degrees F.

Dr. Coley tried to duplicate the fevers with *Streptococcus pyogenes* bacterial lysates, which contained the pyrogenic material lipopolysaccharide (LPS). Coley treated a wide variety of carcinomas and sarcomas with his Mixed Bacterial Toxins (MBT), achieving 5-year survival rates of 60% in inoperable malignant melanoma cases. These rates are considerably higher than those obtained using surgery, radiation, and chemotherapy programs. Problems developed when patients began producing large quantities of neutralizing antibody which required larger amounts of MBT. In addition, Coley had difficulty standardizing the pyrogenicity of the toxins. Coley remained convinced that a key portion of his treatment's success was based due to the enhanced immune response to the toxins, which somehow was cross-reactive against the tumors. Current knowledge of immunology confirms Coley's hypothesis, but it is now clear that antiviral immunity is much more closely related to antitumor immunity than the antibacterial response mechanisms.

This is due to the fact that bacterial infections primarily stimulate the humoral or antibody+complement arm of the immune system. For extracellular parasites such as bacteria and protozoa, this provides an efficient means of elimination within the bloodstream. Viruses, however, are intracellular parasites, and virally-infected host cells express viral antigens on their cell surface in conjunction with normal cell proteins. Hence, Killer Lymphocytes, with ability to recognize and kill virally-infected cells are needed to eradicate the virus. Because cancerous cells also express "self" or normal host antigens on the cell surface along with "non-self" or mutated tumor antigens, the same effector cells: Natural Killer (NK), Lymphokine-Activated Killer (LAK), and antigen-specific Cytotoxic T Lymphocytes, have the primary responsibility of antitumor and antiviral surveillance and elimination. To date, there is no reference in the Scientific Literature to using a pyrogenic virus to induce whole-body hyperthermia.

Other techniques of inducing hyperthermia have been tried: immersion in hot liquids, limb perfusion, and even microwave radiation. The main disadvantage to these methods is that most cancers are deep within the tissue layers, and heating from the outside cannot generate a sufficient temperature to kill the tumor cells. Another problem with these prior-art approaches is that in metastasized cancer, tumor cells are spread throughout the body, and a treatment designed to be curative must heat the entire body as well. A whole-body pyremia approach utilizing a safe but pyrogenic virus solves these two difficulties.

Numerous versions of immunotherapy have been tried in cancer treatment, both specific and non-specific in nature. The primary non-specific immune modulator in cancer therapy has been Bacillus Calmette-Guerin, or BCG. BCG produces a Delayed-Type-Hypersensitivity (DTH) reaction which activates local macrophages to become tumorcidal in some cases. However, it is a poor pyrogenic agent, so hyperthermic benefits are not realized. Also, as detailed previously, it stimulates primarily the humoral arm of the immune system, so interferon production and NK activation are generally low.

Exogenous interferon therapies have been attempted, but suffer from purification and toxicity problems. Researchers have been able to achieve alpha-interferon levels 10 times greater than normal, but the response is hampered by Serum Blocking Factors (SBF) which neutralize the foreign interferon before it can induce a strong cellular response. Immunologists are in general agreement that therapies which stimulate endogenous interferon production are preferable to those which rely on injection of recombinant interferons and interleukins. The described immunotherapy stimulates endogenous interferon A levels approximately 260 times normal levels.

Numerous approaches to cancer vaccines have been attempted, with both sub-unit peptide and whole cell irradiated preparations generating a measurable response. In the case of malignant melanoma, polypeptide vaccines containing a common melanoma antigen: gp100, MART-1/Melan-A, and TRP-1, (Tyrosinase-Related Protein), have been clinically tested. The major drawback to these approaches is that being polypeptides, they provoke a stronger antibody that Killer Cell response. In addition, not all melanoma cells express these antigens in vivo to label them for identification and lysis by effector cells.

Another antigen-specific approach is to use whole cancer cells which have been killed in a manner (usually irradiation) that leaves their antigenic structure intact. These cells are then injected back into the body to induce an immune response. The problem with this approach is that the tumor burden must be reduced by physical means before the specific Cytotoxic T Lymphocytes are induced. The three major anticancer therapies: surgery, radiation, and chemotherapy reduce tumor burden but simultaneously devastate the immune system. The described immunotherapy solves this major problem.

Objects and Advantages

Accordingly, besides the objects and advantages of a whole-body, hyperthermic therapy based on pyrexia in response to a viral agent, several objects and advantages of the present invention are:

(a) to provide a means of reducing the tumor burden through a physical means (fever) in excess of 103.5 degrees F. which does not impair immune function.

(b) to induce trillions of Natural Killer Lymphocytes to become Lymphokine-Activated Killers (LAK) cells capable of tumorcidal activity.

(c) to induce a clone of Cytotoxic T Lymphocytes (CTL) capable of recognizing and destroying tumor cells bearing specific tumor antigens for the life of the patient.

(d) to accomplish the preceding activities without risk of serious harm to the patient.

Other objectives and advantages will become evident from the following detailed description of the invention and its operation.

DESCRIPTION OF INVENTION

Dengue virus is an RNA virus of the Togavirus Family, subfamily flavivirus. It has an icosahederal geometry, approximately 40–45 nanometers in diameter with two major envelope proteins. The E1 protein or Hemagglutin is very rich in the amino acid glycine, and has a molecular weight of approximately 45,000 daltons. The E2 protein or Neuraminidase is rich in the amino acids alanine, serine, and valine and has a molecular weight or approximately 50,000 daltons. The E3 protein is a transmembrane structure which anchors the E1 and E2 proteins to the viral core proteins. Neutralizing antibodies are primarily directed against the E1 protein.

MATERIALS AND METHODS

Patient criteria.

Male or female subjects with stage I, II, im, or IV malignant melanoma or other carcinomas or sarcomas.

Virus

Dengue Virus (available at Walter Reed Army Hospital, Washington, D.C.) passaged in African Green Monkey Kidney cells to less than 5 plaque-forming units /ml. DBS-FRhL-2 roller flasks then are inoculated with seed virus at a minimum of infection or MOI of 0.0005. After adsorption for 1.5 hrs. at 35 degrees C., the inoculum is removed and flasks are washed three times with 100 ml of Hanks balanced salt solution (HBSS). Maintenance medium (200 ml per roller) consisting of Eagle minimal essential medium with 0.25% human serum albumin, 0.22%NaHCO3, streptomycin (50 ug/ml), and neomycin (100 ug/ml). Medium on all flasks changed by day 4, and supernatant fluids harvested on day 6. Before centrifugation at 1,050×g for 20 min., human senum albumin to be added resulting in a final concentration of 2.75%. Albumin pH to be adjusted to 7.6 before addition to the viral fluids. As a final step in clarification, fluid to be filtered through a 0.45 micrometer membrane filter (Nalge, Rochester, N.Y.) Samples are then to be tested for adventitious microbial agents to be performed as described in Public Health Service regulations for licensed, live-attenuated viral vaccines (Code of Federal Regulations, Chapter 21, subchapter F, Biologics).

After removal of samples for testing and plaque assay, remaining volume to be held in ice baths in a 4 degree C. refrigerator for 7 days pending results of safety testing and plaque assays. A final pool of virus to be made from fluids from flasks containing less than 5 plaque-forming units/ml at 39.3 degrees C., and no detectable large-plaque virus present. Average titer for vials to be 850,000 PFU/ml, then freeze-dried for use after neurovirulence testing. Intraspinal and intracerebral bihemispheric inoculation of 0.5 ml virus fluid of male rhesus monkeys with 2 controls receiving virus-free culture fluids. Monkeys to be observed daily for 20 days for evidence of CNS involvement or other physical abnormalities. Following sacrifice, histological examination of lumbar and cervical cord, lower and upper medulla oblongata, mesencephalon, and motor cortex to be made for viral pathology.

Autologous Malignant Cell Preparation.

Melanoma or other neoplastic cells to be surgically dissected, washed 3 times in Earle's Balanced Salt Solution (EBSS), trimmed of fat, normal and necrotic tissue, and finely minced. Resulting cells to be washed with EBSS, concentrations then to be adjusted to 20 million viable cells/ml of Eagle's (MEM) with 10% Fetal Calf Serum (FCS) and 10% dimethyl sulfoxide, frozen at 1 degree C./min, and stored in liquid nitrogen until ready for use. Cultures to contain approximately 20 million viable melanoma or other neoplastic cells determined by trypan blue exclusion. Immediately before use, cells to be irradiated at room temperature with 10,000 rads from a Cobalt 60 source.

Inoculation

Patients to be injected subdermally with 2 ml of viral sample fluids once in each limb, and once at the primary melanoma tumor site. After 3–5 days post-inoculation, patients to be inoculated with autologous irradiated cancer cells subdermally at each primary virus inoculation point. Continued inoculations to be performed every 2 weeks until patient no longer exhibits disease symptoms.

Patient Management

Patients to be completely monitored biomedically: (pulse, blood pressure, respiration, urinary output, and especially body temperature). Patients to be kept well-hydrated and on soft or liquid (high-protein) diet during febrile period. In the case of melanoma, an external heat (electric pad) to be applied directly to visible tumors during febrile period. No antipyretic analgesics to be given as a primary goal of this invention is to achieve a sustained pyremia in excess of 39.5 degrees C. After return to normal body temperature, patients to be discharged and monitored on outpatient basis.

SUMMARY OF INVENTION

In accordance with the present invention a process of destroying cancer cells in a hunan body through whole-body hyperthermia and nonspecific imumne activation brought on by injection of dengue fever virus and and irradiated tumor cells to induce a clone of specific Cytotoxic T Lymphocyte cell line capable of recognizing and killing cancerous cells for the life of the patient.

OPERATION OF INVENTION a. Hyperthermia and thermosensitivity of cancer cells

Cancer cells are more susceptible to heat than normal tissue cells due to many factors:

1. Tumor Type
2. Tumor Location
3. Blood Supply
4. Growth Rate
5. Intracellular pH
6. Cellular Metabolic Level Generally speaking, tumors arising from connective tissue (bone, cartilage, muscle) called sarcomas are more susceptible to hyperthermia than tumors arising from lining or epithelial tissue called carcinomas. This is primarily due to the relative blood supplies of the tissue types. Epithelial tissue has a much richer blood supply than connective tissue, so carcinomas are more thermoresistant. Blood cancers such as leukemias and lymphomas are not susceptible to heat damage. Malignant melanoma share characteristics of carcinomas (it arises from a lining tissue) and sarcomas (it has a poor blood supply).

The location is also critical, as limb tumors are easier to subject to selective heating than those in the body core. Most prior-art hyperthermic successes have been with limb perfusion of sarcomas. Tumors near an extensive network of arterioles are less sensitive than those far away from these main blood vessels.

The relative growth rate of the tumor is also critical. An aggressive, fast-growing tumor needs a richer blood supply than a dormant one. Fast-growing tumors also build up large pools of acidic metabolites, and this factor becomes critical during hyperthermia. At high temperatures, the spindle apparatus which stabilizes chromosomes during their replication is subject to denaturation and collapse, leading to cell death.

At moderate levels of hyperthermia (103.5–106 degrees F.), or (39.5–41 degrees C.) such as are induced by dengue fever, thermosensitivity is primarily due to indirect factors such as blood supply, intracellular pH, and cellular metabolism rates. Tumors have generally poor blood supply because they arise from a single cell, and soon outstrip the local blood supply. Secretion of a hormone called angiotensinogen encourages local blood vessel proliferation, but demand outpaces perfusion rates. In moderate to large tumors, the interior core is dead due to inability to obtain Oxygen, glucose, and other nutrients. Only the outer tumor cells are able to carry out sufficient gas and nutrient exchange for survival.

Tumors also have a lower intracellular pH than healthy tissue due to low perfusion to carry away toxic, acidic by-products of metabolism. Cells have two routes to generate the AdenosineTriPhosphate (ATP) currency molecules used to carry out functional reactions: Aerobic Metabolism and Glycolysis. Aerobic Metabolism uses oxygen and yields 36 ATP molecules per glucose molecule, with little acidic waste products. Glycolysis, on the other hand, is much faster, but yields only 2 ATP per glucose and produces lactic acid, which lowers intracellular pH.

Tumors have higher glycolysis rates than healthy cells because of their excessive growth. Thus, the tumor microenvironment is characterized by hypoxia (low Oxygen), acidosis, and nutrient deprivation. The stage is set for exploiting these weaknesses through hyperthermia.

When body temperature rises, so do cellular metabolism rates. Since enzymatic reactions generally increase as a function of temperature, cells must take in more nutrients and flush away their toxic wastes. Healthy cells, having all their original utility connections intact, can easily stand temperatures of up to 41 degrees C. Tumor cells, on the other hand, are presented with a lose-lose scenario. If they do not increase their glycolysis rate, they will starve. If they do increase their glycolysis rate, their intracellular pH will fall until it reaches 6.7, almost a full logarithmic point below bloodstream pH. At 6.7, the enzymes responsible for critical cell reactions begin to fail, especially the Na-K ATPase pump system. This enzyme is responsible for maintaining the relative gradient of sodium and potassium ions across the cell membrane. When it fails, sodium ions flood in, and the cell dies.

Tumor sensitivity is both time and temperature-dependent, according to the reaction:

s=Soe-kt where s is survival at any given time t and So is survival at initial time and k is a constant representing inactivation rate at given temperature and t is the duration of incubation.

As can be seen from the above equation, cell survival decreases logarithmically. In simple terms, the higher the temperature, the shorter the time period needed for a 1 log or 90% tumor kill rate, a 2 log or 99% kill rate, or a 3 log, or 99.9% kill rate.

Dengue fever produces temperatures sufficient to produce a 1–2 log reduction in viable tumor cells in the case of malignant melanoma, but some cells will survive if they are fortunate enough to have a rich blood supply. It is now up to the immune response to identify and eliminate the remaining tumor cells.

b. Active non-specific immunotherapy operation of invention

Dengue fever virus infects and reproduces in two kinds of white blood cells: immature monocytes (which mature into macrophages), and B-Lymphocytes, which mature into antibody-producing Plasma Cells. In the first three days on infection, dengue kills 60% of the circulating white blood cells, dropping WBC counts from 5300/ml to 2200/ml. When ruptured, these cells liberate massive amounts of interferon, interleukins, and lymphocyte structural proteins into the bloodstream. These lymphokines stimulate NK cells to become LAK cells, which are capable to killing viral-and tumor-antigen expressing cells without regard to specificity. In previous in vitro experiments, dengue-activated LAK cells killed cells of the human tumor line K562 to a high degree. LAK cells are capable of killing tumor cells that are resistant to NK cells, and this is a critical factor in the operation of the invention.

Dengue also induces mature macrophages to become tumorcidal through a lymphokine called MAF or Macrophage Activation Factor. In this state, macrophages become Tumor-Infiltrating Leukocytes capable of killing cancerous cells. Even though this response, following a 1–2 log kill through hyperthermia, may very well eradicate tumor cells from a patient, yielding a cure, it will eventually subside. To be completely certain that no cancer cell survives the heat and the LAK/TIL response, a third component, one that provides for lifelong anti-tumor surveillance and killing capability, is required.

c. Specific anti-tumor response of invention

LAK and TIL cells , while possessing formidable tumorcidal properties, have no immunological memory. After interferon levels return to normal, these nonspecific killer cells have no capacity for “remembering” the antigenic structure that triggered them to destroy a cell. That fiction of the immune system is delegated to the antibody arm of the humoral immunity, and to the Cytotoxic T Lymphocytes.

Cytotoxic T Lymphocytes express cellular determinant antigens OKT3+ and OKT8+, and are OKT4−. These cells are generated in response primarily to viral infections, and are restricted as to MHC lysis capability. This means that they can only recognize and kill cells which express “self” MajorHistoCompatibility Complex proteins in conjunction with altered or “non-self” antigens of cancerous (mutated) or viral origins. These CTL are memory-competent and can identify and kill cells expressing their target antigens for the lifetime of the patient.

Many cancer researchers have attempted to generate tumor-specific CTL with limited success. This is due to weak immunomodulators (BCG), or peptide sub-unit vaccines that induce CTL with narrow cross-reactivity ranges. The therapy described here solves these problems by using an extremely potent immunomodulator (dengue virus), along with inoculation of autologous irradiated cancer cells. This will produce a highly stimulated, large CTL population capable of lifelong memory and broad cross-reactivity among cells expressing antigens derived from the initial tumor line. With nonspecific Effector/Target (E/T) ratios of 100–5,000 to one, and specific E/T ratios of 50–2,000 to one, the therapy should reasonably achieve the goal of eliminating tumor cells from the body as well as preventing their reoccurrence.

Conclusion, Ramifications, and Scope

Accordingly, the reader will see that the combined therapy previously described provides a safe and effective means for eliminating cancer cells from a human body. By combining three methods known to medicine as beneficial to cancer patients, the therapy solves the dilemma posed by current chemotherapy, radiation, and surgery. The above and various other objects and advantages of the present invention are achieved without undue risk to the patient, as full-strength wild-type dengue virus has a mortality rate given by various Tropical Medicine texts as nil, nonexistent, and 1 in 61,000. No other reference to injecting volunteers with any other full-strength virus could be found in any journal.

Although the description above contains many specificities, these should not be construed as limiting the scope of the invention but as merely providing illustrations of some of the presently preferred embodiments of this invention.

Thus the scope of this invention should be determined by the appended claims and their legal equivalents, rather than by the examples given.

Unless defined otherwise, all technical and scientific terms used herein have the same meaning as commonly understood by one of ordinary skill in the art to which this invention belongs. Although any materials and methods similar or equivalent to those described herein can be used in the practice or in vitro and in vivo testing of the present invention, the preferred methods and materials are described. All publications mentioned hereunder are incorporated herein by reference. Unless mentioned otherwise, the techniques employed herein are standard methodologies well known to one of ordinary skill in the art.

The term "substantially pure" as used herein means as pure as can be obtained by standard purification techniques.

I claim:

1. A method of inducing a non-specific immune response in a cancer patient with a sarcoma or melanoma, comprising the steps of:

injecting said patient with substantially pure Dengue Virus; and maintaining body temperature in excess of 103.5 degrees F. of said patient for a sufficient period of time to induce a non-specific immune response.

2. The method of claim 1 wherein said virus is selected from the group consisting of Dengue Type 1, Type 2, Type 3, and Type 4 Serotypes of the family Togaviridae.

3. The method of claim 1 wherein said substantially pure Dengue Virus is purified by passing said virus though living cells with an active transmembrane gradient; and passing said virus through subhuman primates to confirm the elimination of neurovirulence from the virus.

4. The method of claim 3 wherein said cells with an active transmembrane gradient are African Green Monkey Kidney cells.

5. The method of claim 3 wherein said cells are infected with virus at less than 5 plaque-forming units/ml.

6. The method of claim 1 further comprising injecting said patient with autologous cancer cells, and repeating the injection of said autologous cancer cells until sarcoma or melanoma cancer cells in said cancer patient are reduced.

* * * * *